US007001495B2

(12) United States Patent
Essalik et al.

(10) Patent No.: US 7,001,495 B2
(45) Date of Patent: Feb. 21, 2006

(54) GAS COMPONENT SENSOR FOR GAS OXIDES

(76) Inventors: Abdel Essalik, 1677 Chemin Du Fleuve, St-Romuaid (PQ) (CA) G6W 1Z6; John Currie, 6523 Fallwind La., Bethesda, MD (US) 20817; Howard Rosen, 5756 Royalmount Ave., Montreal, Quebec (CA) H4P 1K5

( * ) Notice: Subject to any disclaimer, the term of this patent is extended or adjusted under 35 U.S.C. 154(b) by 1117 days.

(21) Appl. No.: 09/917,072

(22) Filed: Jul. 26, 2001

(65) Prior Publication Data

US 2001/0042684 A1     Nov. 22, 2001

Related U.S. Application Data

(63) Continuation-in-part of application No. 09/498,211, filed on Feb. 4, 2000, now Pat. No. 6,270,651.

(51) Int. Cl.
    *G01N 27/407*   (2006.01)
(52) U.S. Cl. ................. 204/424; 205/781; 252/62.2
(58) Field of Classification Search ........ 204/424–429; 205/783.5, 784, 784.5, 785, 781; 252/62.2; 429/30, 33
    See application file for complete search history.

(56) References Cited

U.S. PATENT DOCUMENTS

| 4,388,155 | A |  | 6/1983 | Chamberland et al. |
| 4,715,944 | A |  | 12/1987 | Yanagida et al. |
| 5,344,546 | A | * | 9/1994 | Kiesele et al. ............... 204/412 |
| 5,589,296 | A |  | 12/1996 | Iwamoto et al. |
| 5,755,940 | A |  | 5/1998 | Shindo |
| 6,143,165 | A | * | 11/2000 | Kurosawa et al. .......... 204/424 |

OTHER PUBLICATIONS

Guth et al., DD 234,335, 1986 (CAS abstract only).*
Essalik et al (Study of a new solid electrolyte thin film micropotentiometric carbon dioxide gas sensor, J. New Mat. Electrochemical Systems, 1, 67-70 (1998)), month not known.
E-Tek Catalog, posted by E-Tek, Inc., May 24, 2001, 5 pages.
Minami, J. Am. Ceram. Soc. 1977, 60, 476, fig 1 only, month not known.

* cited by examiner

*Primary Examiner*—Kaj K. Olsen

(57) ABSTRACT

The present invention is a gas component sensor comprising novel electrolyte compositions. The electrolyte compositions in bulk, sintered or thin film embodiments are capable of forming with different-metal sensing and reference electrodes a highly stable gas oxide sensors. The novel electrolyte composition changes electrochemical reactions at the sensing and reference electrodes and the overall reaction of the electrodes and electrolyte. The novel electrolyte compositions have: (1) excellent chemical stability and thermal compatibility as to the electrodes and a preferred ceramic substrate, (2) excellent chemical stability with the environment as to the reference and sensing electrodes, which need not be sealed against the atmosphere to be sensed, (3) effective adherence to the substrate and electrode metals.

8 Claims, 7 Drawing Sheets

GAS COMPONENT SENSOR FOR GAS OXIDES

This application is a continuation in part of U.S. patent application Ser. No. 09/498,211 filed Feb. 4, 2000, now U.S. Pat. No. 6,270,651 issued Aug. 7, 2001.

BACKGROUND OF THE INVENTION

The present invention relates to dual layer membranes for selectively admitting gas components to gas component sensors.

Prior art electrolytic sensors for carbon dioxide have disclosed the following useful relationship. As disclosed in "Study of a new solid electrolyte thin film based micropotentiometric carbon dioxide gas sensor" (A. Essalik et al, J. New Mat. Electrochem. Systems 1, p. 67–70 (1998)) electrode reactions giving the EMF of such a sensor are as follows:

sensing electrode:

$$1/2\ O_2 + 2e^- + 2\ Na^+ \Leftrightarrow Na_2O$$

$$CO_2 + Na_2O \Leftrightarrow Na_2CO_3$$

reference electrode:

$$Ag \Leftrightarrow Ag^+ + 1e^-$$

where $Na^+$ and $Ag^+$ are the mobile ions and $Na_2O$ and $Na_2CO_3$ are in solid state. The cell EMF can be written according to the Nernst equation as:

$$EMF = K - [(2.3^{RT} Log a_{Ag+})/F] + [(2.3^{RT} Log P_{O2})/4F] + [(2.3^{RT} Log P_{CO2})/2F]$$

where K is a constant, F and R are the Faraday and gas constants respectively and T is the temperature. According to this equation, at constant $P_{O2}$ and silver-ion activity $a_{Ag+}$, the EMF depends only on the CO2 partial pressure.

Also disclosed therein is an inherent restriction on the usefulness of that prior art electrode. "However, for practical use, stability of the sensors should be improved." (Essalik et al, p. 70) and the article explained that the sensor lasted only a few hours at operating temperature. This limitation is a common problem of prior art electrolyte based carbon dioxide sensors. Typically, in other prior art carbon dioxide sensors, high temperature operation (400–500° C.) has been required, although the Essalik et al sensor displayed superior operational response at about 250° C.

There is a need for a carbon dioxide sensor after the Essalik et al device for which stable operation is maintained over a long period of time, sufficiently long for application to control or sensing systems wherein low power, low temperature carbon dioxide sensing may used to advantage.

SUMMARY OF THE INVENTION

The present invention is an electrolyte composition. The electrolyte composition in bulk, sintered or thin film embodiments are capable of forming with different-metal sensing and reference electrodes a highly stable carbon dioxide sensor. The sensor of Essalik et al is improved with changed electrolyte composition, thereby changing the electrochemical reactions at the sensing and reference electrodes and the overall reaction of the electrodes and electrolyte.

The novel electrolyte has: (1) excellent chemical stability and thermal compatibility as to the electrodes and a preferred ceramic substrate, (2) excellent chemical stability with the environment as to the reference and sensing electrodes, which need not be sealed against the atmosphere to be sensed, (3) effective adherence to the substrate and electrode metals. The novel electrolyte has solved the stability problems of the Essalik et al sensor.

The invention electrolyte comprises a relatively small amount of reference electrode metal halide and optionally an alkaline. The invention sensor comprises an electrochemically effective amount of the electrolyte in electrical connection with sensing and reference electrodes, whereby the sensing and reference electrodes are of different metals.

The invention electrolyte has been additionally found to have gas concentration reactive sensitivity to NOx, SOx, H2S, chloride ions, flouride ions and bromide ions. Although insensitive and non-reactive with carbon monoxide, gas concentration carbon monoxide may be indirectly determined by its calculation from the gas concentrations of carbon dioxide and/or nitrogen oxides and sulfur oxides, as the gas species and concentration ranges of a sensed gas are typically known for a specific application of the invention sensor.

The invention electrolyte is effective in bulk or thin layer for chemical specie detection, although the thin layer embodiment has a somewhat lower power requirement and improved response time.

In one embodiment of the invention sensor, a hydrophobic layer filter substantially excludes water from the sensed gas reaching the sensor. Such filters are effective in selecting out or permitting in some chemical species such as water, carbon monoxide, and oxides of nitrogen and sulfur. Where such filters are effectively used, separate invention sensors may be used as an array to determine a profile of multiple gas components in a sensed gas, thereby providing a process determination to recording, control and/or display means. For example, such a profile for a gas composition as air after combustion with oxidizeable components and compared with a prior air composition will indicate the presence of a fire or other undesirable condition. Increased carbon dioxide, oxides of sulfur and nitrogen and carbon monoxide in air typically indicate high temperatures and combustion products.

In a preferred embodiment of the invention sensor, thin layer sensing and reference electrodes are in effective connection through the invention electrolyte, the assembly adhered to a top side of a thin ceramic layer also comprising a resistive temperature detector (RTD), whereby a heating layer is adhered to a bottom side of the thin ceramic layer. As described above, a change in the gas concentration of the sensed component changes the EMF across the electrodes, thereby permitting direct or indirect calculation of the concentration of the sensed component. The invention sensor in this embodiment is inexpensive, easy to fabricate, compact, operates at low temperature, and uses very low power. The small size and low power use of the invention sensor enable the skilled person to now use a stable carbon dioxide sensor in low power and temperature sensitive assemblies. The invention sensor has a broad operating range as to carbon dioxide, typically up to and exceeding 10,000 ppm. Such a range of operation allows use of the invention sensor in devices for sensing, recording or controlling air quality, fire detection, chemical, biochemical and biological (including medical) processes, agricultural processes and the like. The present sensor senses a sensed component independent of the flow rate of the component across the sensor. The present sensor eliminates gas tight sealing of at least one electrodes against a sensed or reference gas. The present sensor now permits stable operation through a substantially equilibrium reaction at the electrolyte/reference metal interface of the following reaction:

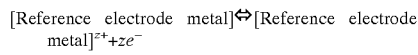

The above benefits were not realized or taught in the prior art with respect to the novel electrolyte composition of the invention. The invention electrolyte comprises electrochemically effective amounts of one or more alkali metal carbonates, one or more alkaline earth metal carbonates, one or more reference electrode metal halogens and optionally an amount of one or more alkali halogens. Although not specifically described herein, the invention electrolyte may comprise substantially electrochemically neutral components while still achieving the objects of the invention. Thus, a description of the invention electrolyte will include a composition with such substantially neutral components so long as the invention benefits are obtained with an electrochemically effective amount of the electrolyte applied across the electrodes of the invention sensor.

The invention electrolyte also comprises a method for conversion from a carbon dioxide sensing electrode to an electrode capable of sensing oxides of nitrogen or sulfur or hydrogen sulfide. At operating temperature, the invention electrode is exposed to substantial amounts of oxides of nitrogen or sulfur or hydrogen sulfide, resulting in absorption and reaction of a portion of that component with the invention CO2 electrolyte. The resulting electrolyte (such as including sodium or barium nitrate or sulfate) thereby becomes sensitized to that component in addition to some sensitivity to carbon dioxide. Calculation of the concentrations of the sensed components is possible from a previously determined potential range of component concentrations for carbon dioxide and the other component, or a filter may be arranged such that substantially all carbon dioxide is excluded from the sensed gas.

DETAILED DESCRIPTION OF THE INVENTION

The invention electrolyte comprises the following specific ranges of electrochemically effective components relative to each other in weight percent:
  alkali metal carbonate(s): from about 20% to about 99%;
  alkaline earth metal carbonate(s): from about 20% to about 99%;
  reference electrode metal halogen(s): from an electrochemically effective amount, but most preferably from about 0.005% to 10%; and
  alkali halogen(s) (optional): about 0.5% to 1.0%.

Exemplary alkali metal carbonate are $NaCO_3$, $Li_2CO_3$, $K_2CO_3$, and $Rb_2CO_3$. Exemplary alkaline earth metal carbonates are $BaCO_3$, $CaCO_3$, and $SrCO_3$. Exemplary reference electrode metal halogens comprise any inorganic salt of the reference electrode metal and halogen ions or oxy-anions as one group or the group of Cl, Br or I. Exemplary alkali halogens are NaX, LiX, KX, and RbX where X is chosen from the group of Cl, Br or I.

Sensing and reference electrode metals are preferably chosen from the group Ru, Rh, Pd, Re, Os, Ir, Pt, or Au. It does not matter which two of the preferred metals are chosen from among this group for the sensing and reference electrode so long as the two metals are different. Optimizing price and ease in fabrication will result in a choice from the above group of sensing and reference electrodes.

For a thin film embodiment of the present invention, it has been found that a ceramic substrate of α-alumina is a preferred material, although many other appropriate supports are appropriate depending on adhesion and heat transfer characteristics of the substrate. A preferred thickness of the ceramic substrate is from about 50 um to less than about 1 millimeter. It is preferred to prepare the surfaces for thin film deposition by cleaning in baths of warm acidic solution (Citronox), warm acetone solution, warm isopropanol solution, and warm deionized water dried in nitrogen gas at about 140° C.

Figure 1:
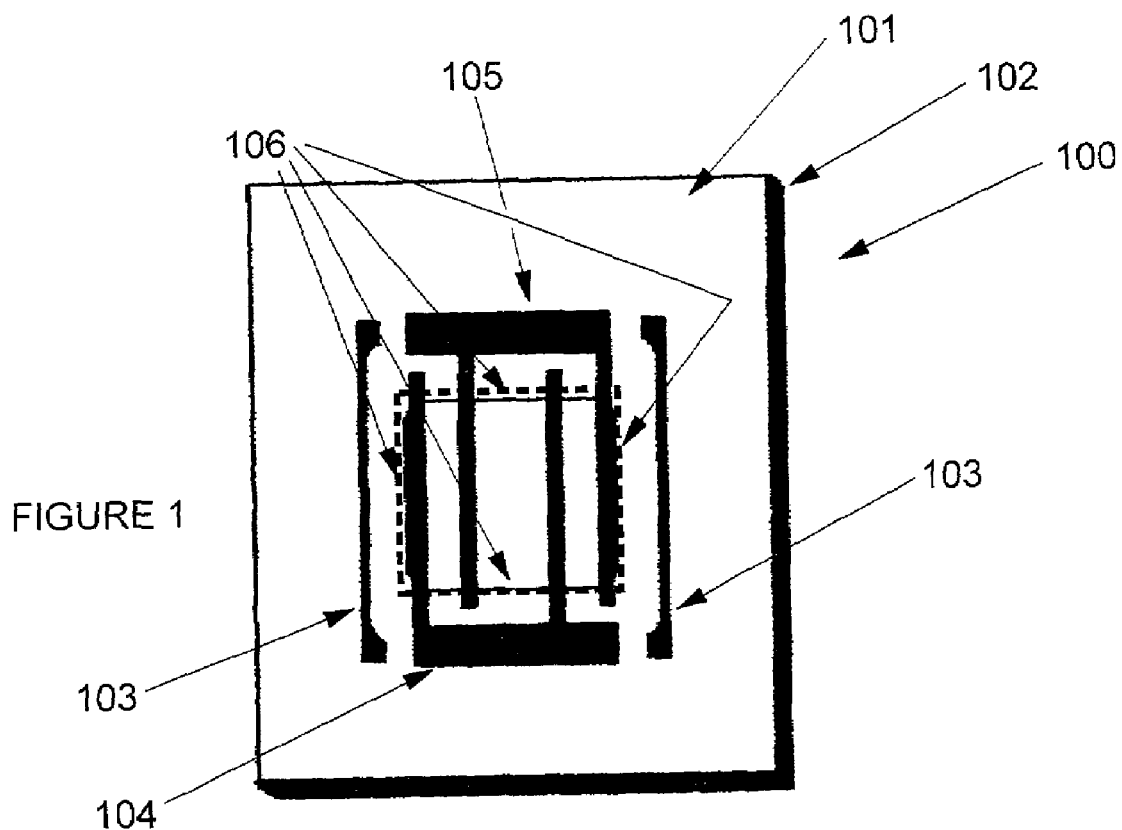
FIG. 1 is a top view of the interdigitated reference and sensing electrodes and RTD's on a top side of a thin support layer, with the outline of the invention electrolyte shown in broken lines.
Figure 2:
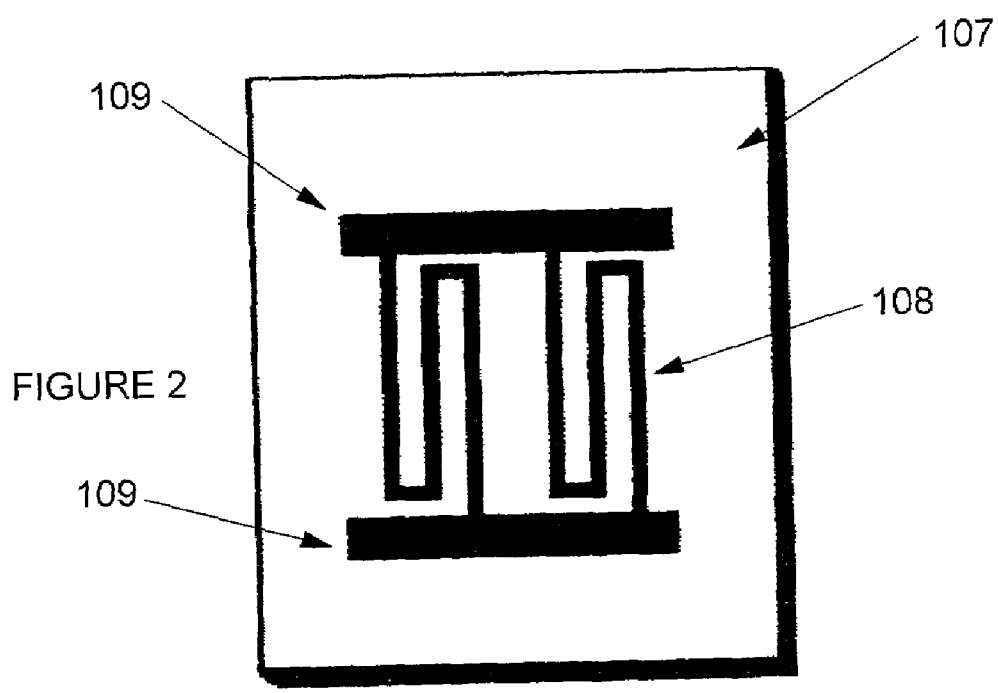
FIG. 2 is a bottom view of a bottom side of the thin support layer, having adhered thereon a resistive heating element.

FIGS. 1 and 2 show a thin film invention sensor assembly 100 having ceramic substrate with a top side 101, thickness 102 and bottom side 107. Sensing electrode 104 is interdigitated with reference electrode 105 between RTD's 103, all of which are applied as thin films to top side 101 via sequential e-beam evaporation and patterned by lift-off. When using Au or Pt for electrodes or otherwise depositing such on the substrate, it is preferable to first deposit a layer of chromium to improve adherence of the thin layer metals. It is preferred that electrode layers have the following thicknesses: Ag/>15000 angstroms; Pt—Cr/>1000 angstroms; Au—Cr/>5000 angstroms.

The RTD's are preferably Pt, as well as the thin film heater 108 having wire connections 109. It is apparent to the skilled person that the embodiment of FIGS. 1 and 2 comprise sites for wire lead attachment for connection to electrodes 104 and 105, RTD's 103 and heater 108. The outline 106 of FIGS. 1 and 2 shows the preferred extent of deposited invention electrolyte on assembly 100, thereby covering a substantial portion of the interdigits of electrodes 104 and 105.

After deposition of the electrodes 104 and 105, electrolyte 106 is deposited in the following manner. A sputter target disk of about 2 inches diameter and 5 millimeter thickness is prepared from the bulk powder form of the invention electrolyte. The disk is prepared similarly to the process of Essalik et al by hydraulic (6,000 psi) and cold isostatic press (40,000 psi). The target was mounted in the RF magnetron sputtering guns in a UHV chamber for low pressure chemical vapor deposition to the thin film. The target was hygroscopic and therefore was maintained in vacuum protected by load lock. The sputtering chamber of the RF magnetron was back-filled with pure argon to a working pressure. Sputtering of the target to the substrate was done at a power level of about 85W at about 1.1 angstroms/s, producing a thin film of about 20,000 angstroms. The outline of the deposited electrolyte is maintained only such that it is substantially electrochemically in touch with opposing edges of the interdigits of electrodes 104 and 105.

The following list are actual examples sputtering target disk compositions for four embodiments of the invention electrolyte incorporated into a CO sensor assembly 100 and having $CO_2$ sensing capabilities according to the performance characteristics described herein:

1. $BaCO_3$, 17.7615 g.; $Na_2CO_3$, 5.2995; AgCl, 0.3583 g.; NaCl, 0.0055 g. or 0.0 g.
2. $NaCO_3$, 17.7615 g.; $Ba_2CO_3$, 5.2995; AgI, 0.5869 g.; NaI, 0.0055 g. or 0.0 g.
3. $Li_2CO_3$, 17.7615 g.; $Ba_2CO_3$, 5.2995; AgCl, 0.3583 g.; NaCl, 0.0055 g. or 0.0 g.
4. $Li_2CO_3$, 17.7615 g.; $Ba_2CO_3$, 5.2995; AgI, 0.3583 g.; NaI, 0.0055 g. or 0.0 g.

Figure 3:
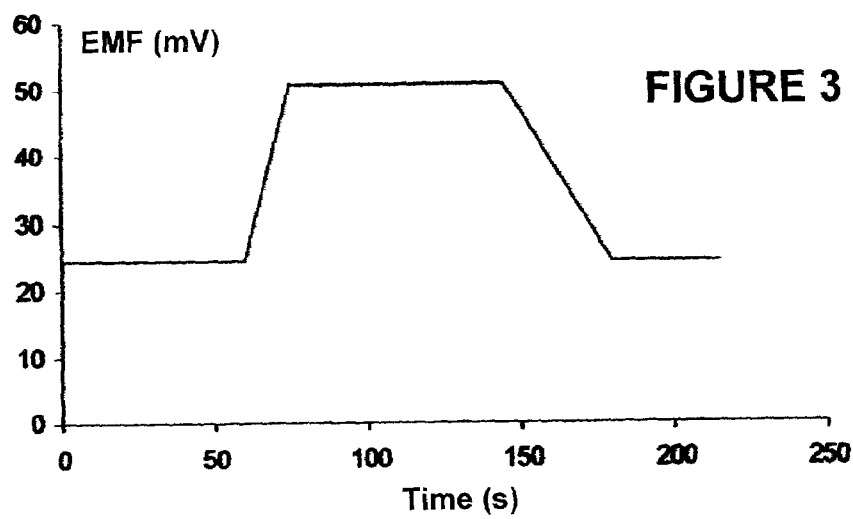
FIG. 3 is a graph of the EMF response of the invention thin film electrolyte to CO2 in a sensed gas.

FIGS. 3–8 show performance characteristics of the sensor assembly 100 wherein heater 108 causes the electrolyte 106 to reach about 250° C. and a higher concentration $CO_2$ containing gas is introduced to and withdrawn from the electrolyte 106 surface. For a single, exemplary sensed gas, FIG. 3 shows that full response time to the higher concentration $CO_2$ containing gas requires only about 20 seconds (from about 65 seconds to 85 seconds) to reach accurate measurement and about 65 seconds to recover once the higher concentration $CO_2$ gas was replaced with the previous gas. In general, the thin film embodiments of assembly 100 comprise sensors for $CO_2$, $NO_2$ and $SO_2$. The results for $CO_2$ sensor assembly 100 at 250° C. were about 45±3 mV/decade sensitivity, 10–30 seconds for response time and around 60 seconds recovery time. The results for $NO_2$ sensor assembly 100 at 250° C. were about 48±3 mV/decade sensitivity, 2–10 seconds for response time and around 10 seconds recovery time. The results for $SO_2$ sensor assembly 100 at 250° C. were about 50±3 mV/decade sensitivity, 1–2 seconds for response time and around 5 seconds recovery time. Exemplary electrolyte compositions for $NO_2$ and $SO_2$ sensor assemblies are respectively: (1) $BaNO_3$, AgCl, and NaCl and (2) $BaSO_4$, $Na_2SO_4$, AgCl, $V_2O_5$, and NaCl. Sputtering target and thin film deposition techniques for $NO_2$ and $SO_2$ sensor assemblies are as above.

A gas sensor for oxides of nitrogen assembly would comprise (a) an electrolyte comprising (i) one or more alkali metal nitrates, (ii) one or more alkaline earth metal nitrates, and (iii) one or more reference electrode metal halogens, wherein the reference electrode metal of the reference electrode metal halogens is chosen from the group consisting of ruthenium, rhodium, palladium, rhenium, osmium, iridium, platinum and gold and the halogens of the reference metal halogens are chlorine, bromine or iodine, (b) the electrolyte in electrochemical connection between a sensing electrode and a reference electrode, whereby the reference electrode consists of a first reference electrode metal and the sensing electrode consists of any other reference electrode metal, and (c) the electrolyte and electrodes are supported on a substrate. Preferably, the concentration of alkali metal nitrates is greater than about 20 weight percent of the total weight of alkali metal nitrates, alkaline earth metal nitrates, and reference electrode metal halogens. Preferably, the concentration of reference electrode metal halogens is greater than about 0.005 weight percent of the total weight of alkali metal nitrates, alkaline earth metal nitrates, and reference electrode metal halogens.

Figure 4:
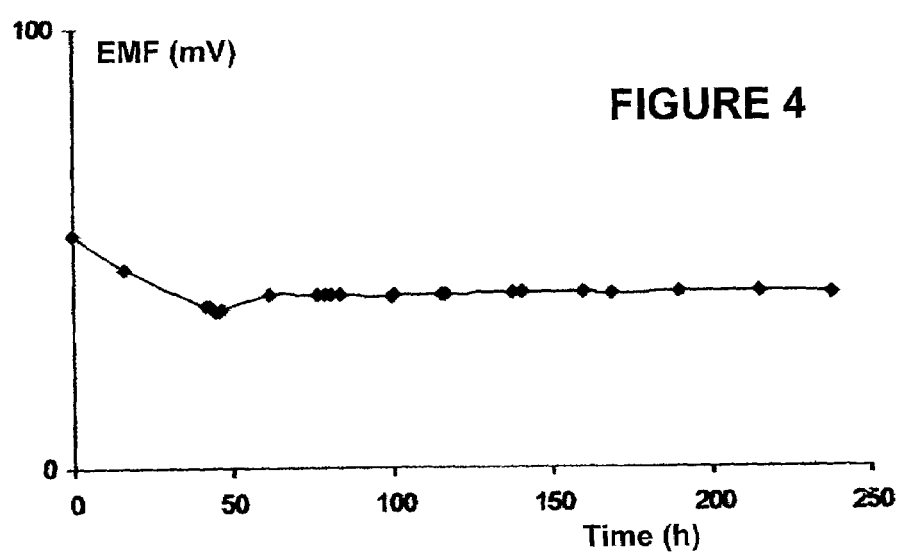
FIG. 4 is a graph demonstrating stability of the invention CO2 sensor.

FIG. 4 is a graph demonstrating stability of the invention $CO_2$ sensor. It easily seen that sensor response is substantially flat after an initial period of decline.

Figure 5:
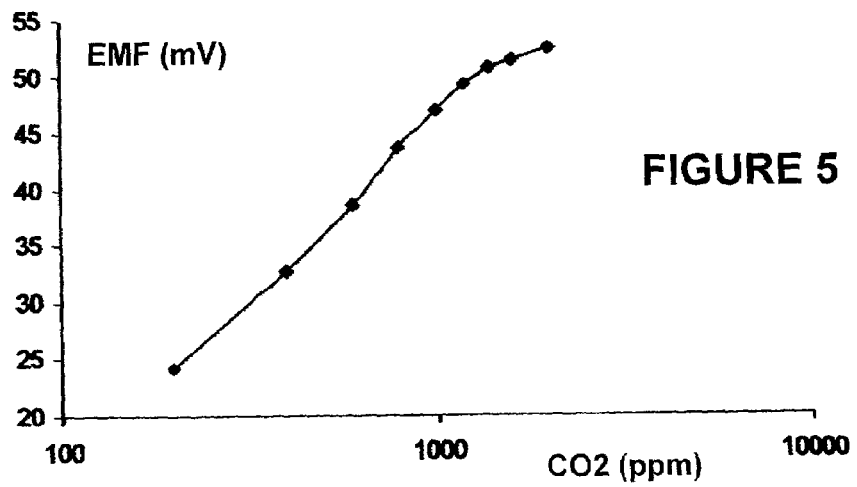
FIG. 5 is a graph demonstrating the response of the invention CO2 sensor to CO2 levels in a gas.

FIG. 5 is a graph demonstrating the response of the invention $CO_2$ sensor to $CO_2$ levels in a gas. The lower $CO_2$ concentration sensitivity at about 2000 ppm and below is especially useful for devices incorporating the $CO_2$ sensor into a display, recording or control system where the gas will come into contact with breathing air of animal life.

Figure 6:
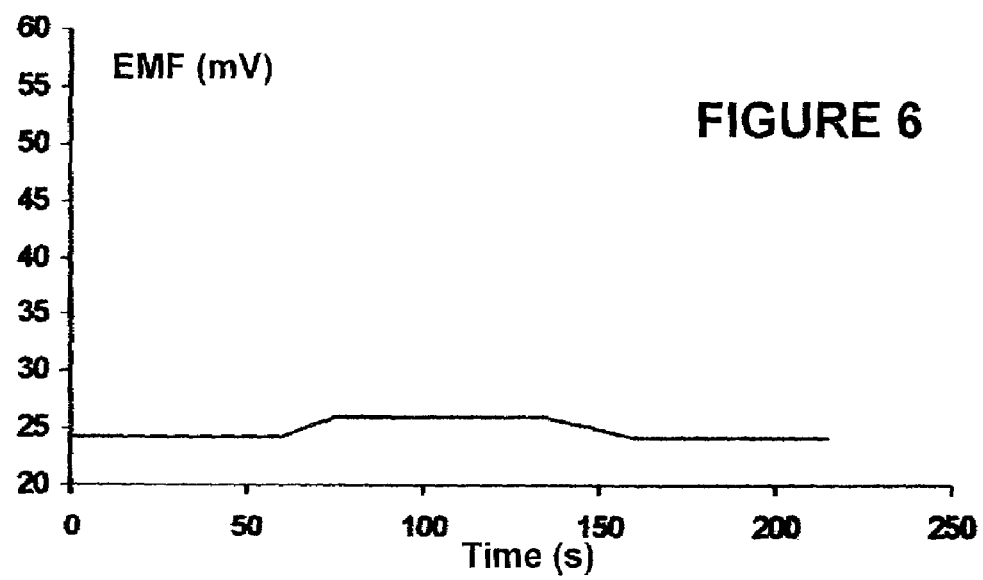
FIG. 6 is a graph of the invention CO2 sensor response to non-CO2 components of air as to the response of the sensor shown in FIG. 5.

FIG. 6 is a graph of the invention $CO_2$ sensor response to non-$CO_2$ components of air as to the response of the sensor shown in FIG. 5.

Figure 7:
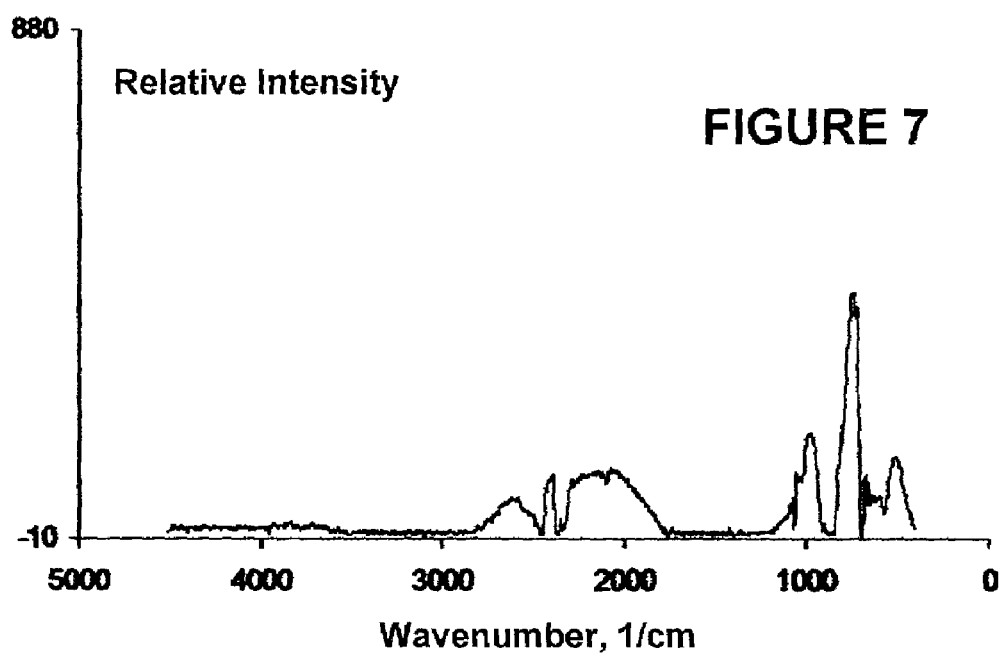
FIG. 7 is an infrared spectra of the bulk invention electrolyte.

FIG. 7 is an infrared spectra of the bulk invention electrolyte.

Figure 8:
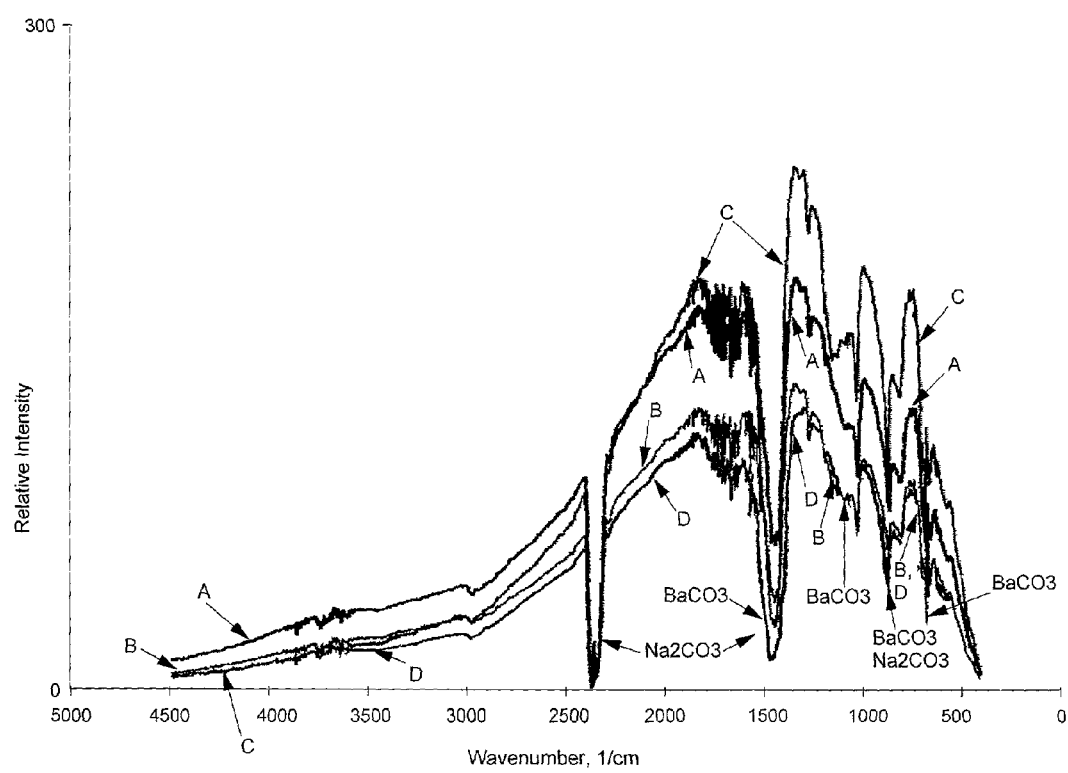
FIG. 8 are the infrared spectra of the bulk and thin film invention electrolyte maintained at 130° C. and 400° C. for 14 days, demonstrating component integrity and continued stability of the invention electrolyte over time.
Figure 9:
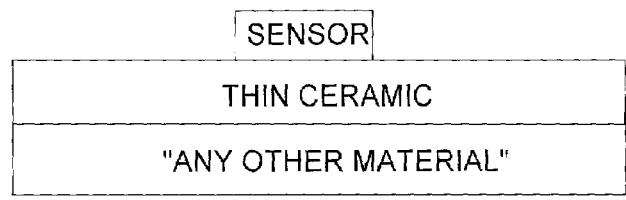
FIG. 9 is a side cutaway view of one embodiment of the electrode.

FIG. 8 are the infrared spectra of the bulk and thin film invention electrolyte maintained at 130° C. and 400° C. for 14 days, demonstrating component integrity and continued stability of the invention electrolyte over time. Component locations on the spectrum are shown in the Figure. Traces A and C show, respectively, bulk powder composition after 14 days of exposure to heating in air at 400° C. and 130° C. Traces B and D show, respectively, thin film composition after 14 days of exposure to heating in air at 130° C. and 400° C. It will be readily appreciated that the powder electrolyte experiences a greater percentage loss of electrochemically effective components in the increase in temperature from 130° C. to 400° C. than the thin film electrolyte. The thin film embodiment of the invention electrolyte remains effective in composition through long periods of exposure to much higher temperatures than required for effective operation.

The specific example of the above thin film $CO_2$ sensor operates effectively with a current of about greater than about 5–10 mA. The low power usage translates into low ambient heat transfer, thereby permitting use in compact, temperature sensitive devices. It is, however, an alternate embodiment of the sensor assembly to do without the RTD's and thin film heater where ambient conditions of a sensed gas are within the temperature range required by the invention sensor assembly.

EMBODIMENT FOR COMPOSITE MEMBRANE FOR PROTECTION OF A GAS SENSOR

The present invention of this embodiment is one of the many forms of gas components sensors in the prior art or to be developed later that are protected from some gas components by a dual layer membrane or a membrane that is effectively made to exhibit properties of such dual layer membranes. Specifically, it is known that electrolyte based gas sensors may impaired by gas components such as water, oxides of nitrogen or sulfur, or other such components. The impairment components typically react to permanently damage the gas sensor abilities or may compete for sensing surface area or sites on the gas sensor. In either case, a gas sensor can require that one or more gas components be excluded for short term or long term sensing stability.

The following discloses prior art gas sensors. Essalik et al (Study of a new solid electrolyte thin film micropotentiometric carbon dioxide gas sensor, J. New Mat. Electrochemical Systems 1, 67–70 (1998) discloses a thin film CO2 sensor with a composition similar to the invention electrolyte without ions of the electrode metal or different electrode metals.

U.S. Pat. No. 4,388,155 discloses a shielded side sensor illustrating the operation problems of exposing both electrodes to the sensed gas.

EP Application 91113350.2 discloses a sensor of the NASICON type requiring specific ratios of alkali metal carbonates to alkaline metal carbonates.

U.S. Pat. No. 5,759,366 discloses a solid electrolyte ceramic with alkali ion conductivity, and two electrodes of conductor material inert with respect to the electrolyte.

U.S. Pat. No. 4,715,944 discloses an allegedly stable operation CO2 sensor having a gas shielding layer with respect to the electrolyte thereby protected.

U.S. Pat. No. 5,910,239 discloses titanium dioxide or tin dioxide used in alkali/alkaline earth metal based electrolyte.

However, gas sensors operate on the principle of gas exchange, i.e., that a volume of gas, typically small, is sensed and is replaced with another volume that is in turn sensed. The volumes exchanged must be representative of the larger volume whose composition is of concern. The requirement of gas exchange has resulted in development of some selective membranes for gas sensors. Selectivity by membrane necessarily slows response over the condition where no membrane is used. Thus, the benefits of selectivity for protection of a gas sensor must be balanced against the capability of the membrane to exchange volumes of gas with the external environment in time for a sensor response to be of use.

The art of membranes for protection of gas sensors has been expanded with the present invention. The present invention is a composite membrane comprising a support layer arranged so that it is bonded to an exclusion layer, the dual layer forming a barrier against an external environment having one or more undesirable gas components. The composite membrane has adequate porosity for required gas volume exchange and is preferably near the gas sensor without an intervening layer. The exclusion layer is applied to the side of the support layer that would be exposed to the external environment.

In a specific embodiment, a general class of composite membranes is disclosed as those dual layer membranes used in fuel cell technology for gas diffusion electrodes, with or without electrocatalyst loading, a commercial embodiment of which is currently sold by E-Tek Inc., a well known provider of fuel cell components to the industry. That commercial product has a porous support layer overlain with Teflon® (PTFE) that has been pressed onto or into the surface of the support layer. The sole uses of this composite membrane in the prior art has been for a liquid to gas interface. The commercial product is disclosed in combination with a system for fuel cells at their Internet web site where they describe their product as an electrode or catalyst (support layer) that can be adhered directly to a polymer electrolyte membrane. The constructions are known to E-Tek, Inc. as membrane electrode assemblies used in fuel cells for power generation. This art of composite membranes has been developed for electrical power generation as a liquid to gas interface since 1930. Although the technology has advanced dramatically, the uses in the prior remain as a liquid to gas interface with uni-directional flow of gas components. No prior art reference suggests their use as an interface for gas to gas where gas exchange back and forth across the membrane occurs. The present invention uses the composite membrane in just such a manner to exclude from a gas sensor a component in the external environment gas.

The support layer of the E-Tek, Inc. composite membrane has a porosity and other characteristics that are designed as a liquid water to gas interface. The exclusion layer of the E-Tek, Inc. composite membrane is shown to be Nafion® or a polymer of the customer's choosing. In preferred embodiment, the exclusion layer is Teflon® to form a hydrophobic layer on the support layer. The composite layer thereby forms a water exclusion dual layer membrane that surprisingly permits sufficient diffusion back and forth across the membrane so that a gas sensor located fairly close to the membrane is protected but is capable of providing a timely response as to the concentration of one or more components in the external environment. Clearly, if one or more gas components are excluded from the gas sensed by a protected sensor, the concentration of the sensed gas component in the protected gas volume is not precisely that of the external environment. If it is likely that this will introduce substantial error in the concentration desired to be known by measurement by the gas sensor, a second sensor for the excluded components may sense them in the external environment and the result directed to a logic means such a computer with the result of the concentration of the desired gas component so that a correction may be made before transmittal to a user of the information.

The E-Tek, Inc. product is a flat and relatively thin support layer having pressed into or onto one side a polymer as an exclusion layer. U.S. Pat. Nos. 5,798,668, 6,130,175, and 6,156,461 disclose fluorinated polymers for both the porous support layer and a hydrophobic exclusion layer.

U.S. Pat. Nos. 5,126,216 and 5,298,343 are directed to a catalyst whose activity as a catalyst is of no particular use to the present invention, although the solid material produced from production of the invention catalysts forms a material useful as support material for the present invention. The prior art discloses some dual layer membranes. U.S. Pat. No. 6,045,697 and the parent patents to it disclose a mineral oxide support with a polymer exclusion layer of PS, PVA, PFV, and others. U.S. Pat. No. 6,048,383 tells of a dual layer membrane with a support layer made of carbon fiber in a thermoset resin or glass fiber in an epoxy and an exclusion layer made of a fluorinated polymer for hydrophobicity.

Figure 10:
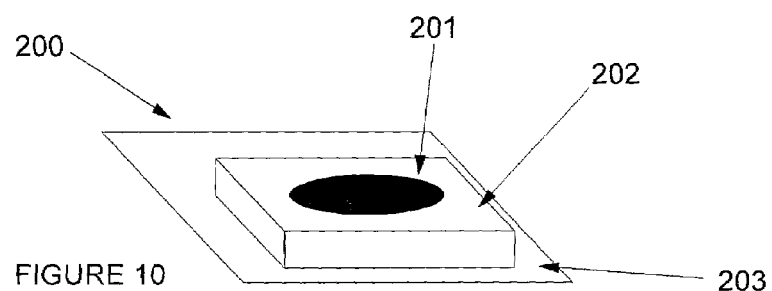
FIG. 10 is a top perspective view of an electrolyte electrode selectively sealed against an outside atmosphere only as to some gas components.
Figure 11:
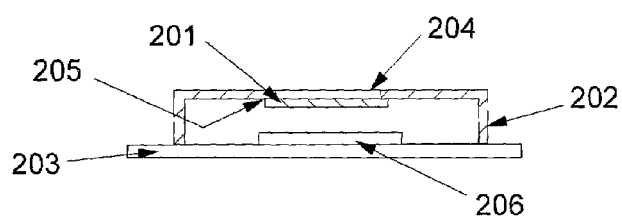
FIG. 11 is a side cutaway view of the device of FIG. 10.
Figure 12:
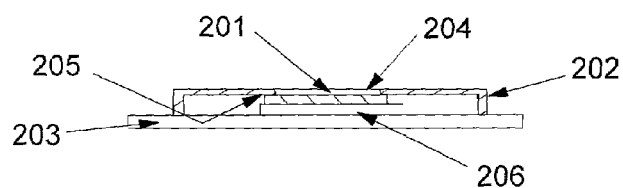
FIG. 12 is a side cutaway view of an alternate embodiment of the device of FIG. 11.

FIGS. 10 and 11/12 are respectively perspective and cut away side views of a specific embodiment of the invention system 200. A base plate 203 has sealingly mounted to it cover 202 which has in its top surface a hole 204 that allows external environment gas to pass to the cavity formed between plate 203 and cover 202. Within that cavity and on the plate 203 is a representative gas sensor 206, such as the above disclosed electrolyte gas sensors or other gas sensors that require gas contact with the sensor. Sensor 206 is open to the external environment except for composite membrane 201 sealed at its periphery 205 to the underside of the top part of cover 202, where the sealing is gas tight so that substantially all gas exchange between the external gas environment and the gas sensor passes back and forth through the composite membrane 201. In a preferred embodiment, the exclusion layer of membrane 201 is adjacent to the underside of the top part of cover 202 so that gas tight sealing between cover 202 and membrane 201 is more easily accomplished and so that the support layer is sealed against the external environment that may have components damaging to the support layer materials. The preferred embodiment of FIGS. 10 and 11 teaches the skilled person by its disclosure that a composite membrane is sealed in a manner that does not permit external environment gas to reach the sensing surface of a gas sensor without first passing through the composite membrane. This means that the composite membrane 201 may contact or be sealed directly to the sensor 206 as in FIG. 12. Fabrication may permit sputtering or other such fabrication of a support layer of a membrane 201 directly on a top surface of a sensor 206 with an exclusion layer applied later to the top surface of the support layer. Alternately, support layers may be applied as the above described polymers or mixtures thereof and the exclusion layer applied thereafter.

Figure 13:
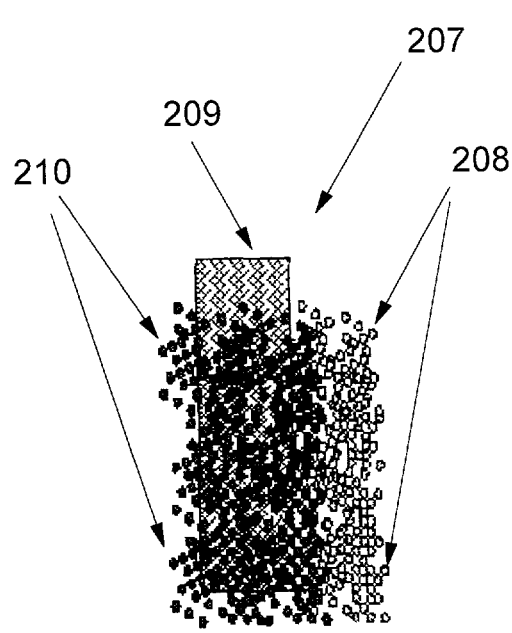
FIG. 13 is a side cutaway view of one type of composite membrane.
Figure 14:
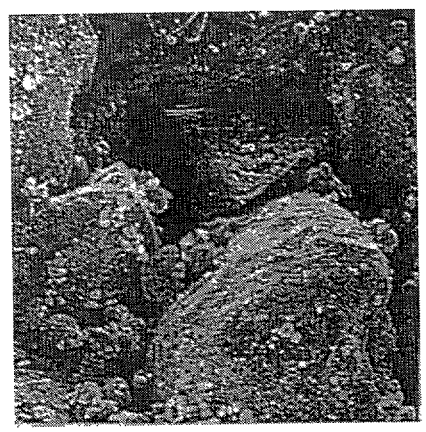
FIG. 14 is a microphotograph of a carbon fiber cloth that can be used as a support in the composite membrane.

In a most dual layer composite membrane, FIG. 13 shows a diagram of a commercial product of E-Tek, Inc. The product A-6 solid polymer electrolyte electrode, single sided version has support layer 209 as a plain weave carbon cloth of 3.4 oz/yd2 (116 g/m2). The support thickness is about 0.36 mm. FIG. 14 is a microphotograph of an exemplary carbon cloth Vulcan XC-72 (Cabot Industries Corp.) used in the support layer of the composite membrane of composite membrane 207. A finished catalyzed electrode ranges from 0.45 mm to 0.50 mm in thickness depending on the catalyst loading 210. Gas-side wet-proofing is by means of a hydrophobic fluorocarbon/carbon layer 208 on one side of cloth only. In the commercial product of FIG. 13, E-Tek, Inc. uses Nafion® as the hydrophobic fluorocarbon for layer 208, which is pressed at high pressure into the support layer 209 to obtain the hydrophobic fluorocarbon/carbon composite. The water exclusive effect of the inventive system may also be provided by other polymer in layer 208, as disclosed in the research of Jochen Kerres et al in the article "DEVELOPMENT OF MEMBRANES FOR ELECTROLYSIS AND MEMBRANE FUEL CELLS" (Institut für Chemische Verfahrenstechnik, Universität Stuttgart, Dec. 24, 1996, Collaborative Research Center SFB 270/Project A7. As is well demonstrated in the prior art, no one heretofore has shown inclination to attempt to use the composite membranes of this embodiment of the invention system in a gas to gas interface for water exclusion. In the composite membrane of FIG. 13, a model is disclosed for preparation of other component exclusive layers, whereby layer 208 is a polymer/carbon composition formed from pressing or combining by other method on to support layer 209 with high porosity and adequate support such as is found in carbon fiber cloth or carbon paper. As for any physicochemical phenomena, the determining step is the slowest step and in this embodiment the slowest step is the diffusion of the gas through the hydrophobic part of the membrane which is equipped with the smallest porosity. It is most preferred where the support layer is at least somewhat hydrophilic that the support layer be sealed from the outside environment by the hydrophobic layer and other structure or materials.

Figure 13A:
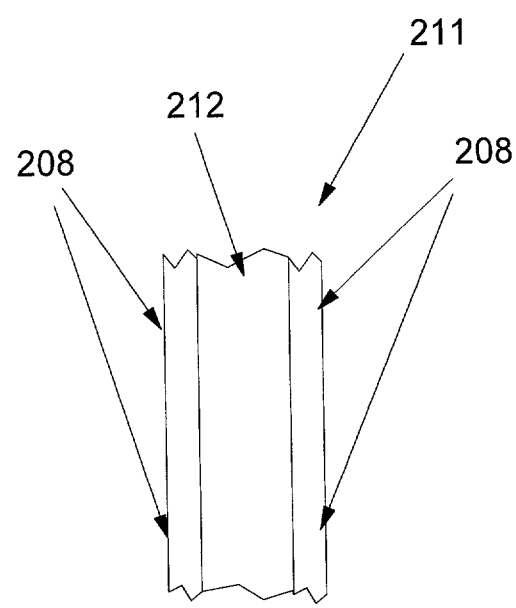
FIG. 13A is a side cutaway view of another type of composite membrane.

FIG. 13A shows an alternate form 211 of a composite membrane. Operation of electrolyte gas sensor typically requires heating to substantially over the vaporization temperature of water. Hydrophilic layers 208 are impressed or adhered to both sides of a dessicant layer 212, although in one form of this embodiment a hydrophilic layer 207 is optionally eliminated from the side of the membrane facing the electrode. Dessicant layer 212 comprises either a dessicant material such as a zeolite or porous silica as the support for the hydrophobic layers 207 or a material such as carbon cloth or other porous material impressed or impregnated with water absorbent but material that results in a porous support layer as in the device of FIG. 13. The composite membrane form 211 of FIG. 13 takes advantage of the heating of the gas sensor to dry the dessicant layer 212. During operation of a heated electrolyte electrode, water molecules are typically not absorbed on the electrolyte in such quantity to seriously affect electrode performance. However, in a non-operation state when the temperature of the electrode is reduced below the vaporization temperature of water, water molecules can absorb into the electrolyte of the electrode at an unacceptable rate and cause long term reduction in gas sensing accuracy. The present composite membrane uses dessicant in layer 212 to capture water molecules. In non-heated states, gas will pass from an atmospheric side of the membrane and through a layer 207 to layer 212 where water will be absorbed. The substantially dry gas will pass directly to the gas sensor or through yet another hydrophilic layer 207 to enhance water molecule retention in the dessicant layer 212. During heated operation, the water molecules in layer 212 are driven off and layer 212 is again ready to capture water molecules in non-heated states. Alternately, heated operation of the gas sensor may be initiated periodically not to specifically to sense a gas concentration but instead to drive off water molecules from the dessicant layer. A dessicant layer may also be used with reduced temperate of the atmospheric gas to cause condensation of water on the dessicant layer and drain means are provided to draw off the condensed water, whereafter heated operation will drive the water off. The dessicant layer thus becomes an effective barrier to water molecule intrusion into an electrolyte gas sensor.

EMBODIMENT FOR DRIFT COMPENSATION WITH DUAL GAS SENSORS

The above invention gas sensors for carbon dioxide exhibit effective lives much in excess of the prior art electrolytic sensors. However, operation of the sensors in some environments indicates that continuous operation at effective temperatures leads to a drift in accurate measurement of carbon dioxide in the measured gas volumes passing across the exposed surface of the electrolyte.

Figure 15:
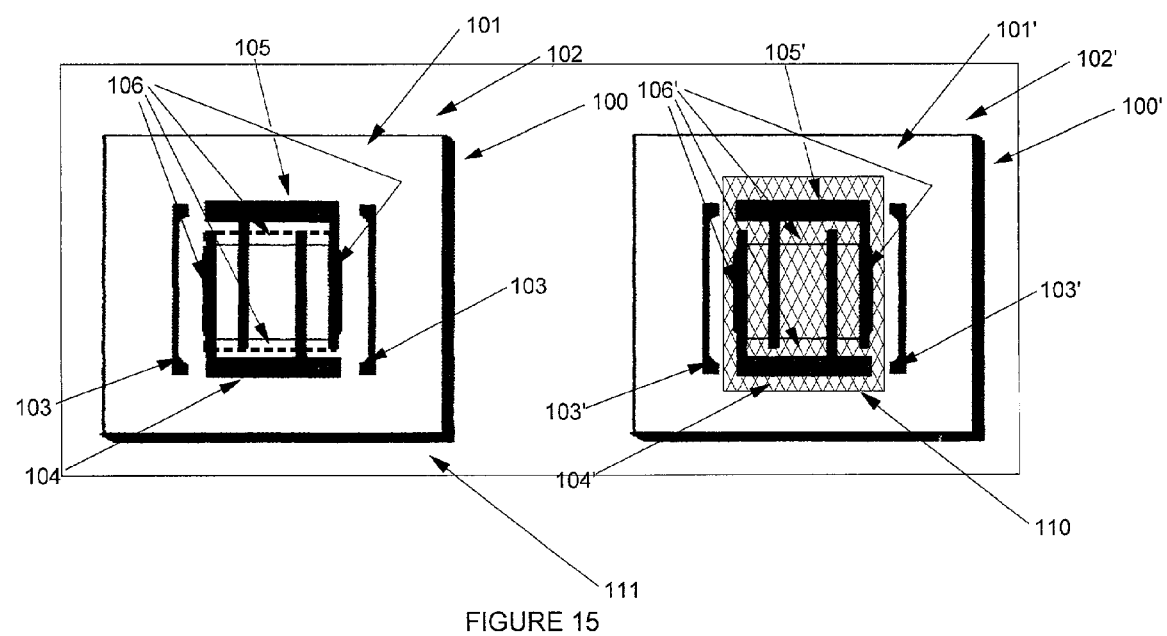
FIG. 15 is a top view of a drift compensating embodiment.

FIG. 15 is a top view of a drift compensating embodiment of the present invention. An invention electrolyte gas sensor 100 as in FIG. 1 is shown in FIG. 15 closely associated with a substantially identically functioning electrolyte gas sensor 100'. The aspect numbers of sensor 100' identify substantially the same structure and function of the aspects of sensor 100, although the prime (') designation with an aspect number indicates the aspect's association with sensor 100'. The support 111 preferably brings sensors 100 and 100' into such close supporting association with effectively about the same heat transfer from a heating element or means that the electrolytes of sensors 100 and 100' experience about the same temperature during operation. Sensor 100' comprises a modification of a gas tight overlay 110 that seals the electrolyte of sensor 100' against the atmosphere. The sealing of the sensor 100' preferably takes place in a typical ambient air atmosphere, although the sealing step may take place in a sensed component-rich or sensed component-absent gas atmosphere.

It has been found that integrated operation of the sensor 100' with one or more sensors 100 at about the same temperature and in effective connection with logic means recording and comparing the potentials across the sensors 100 and 100' results in a substantially constant potential across sensor 100' comparable to reduced potential drift of sensor 100 over a very long period of time. The logic means is programmed to record over a number of short periods the potential across sensor 100, whereby a sequence of relatively constant recorded potentials indicates a period of substantially constant sensed gas concentration of a sensed component. Where the potential of sensor 100 has declined from the start of the period of constant sensed gas concentration of a sensed component to the end of that period, the rate of that decline is compared with the rate of a decline or change, if any, in the potentials across sensor 100' for the same period of time. The logic means uses the overall of instantaneous rate of change of sensor 100 mathematically compared with the overall of instantaneous rate of change of sensor 100' to generate a correction factor which is applied to the current potential from sensor 100 which is then mathematically transformed to a sensed component concentration for use or display in display means such as in a display screen or printed on media from a printer. For example, if no change in potentials occurs across sensor 100' in a 30 hour period but a 10% decline has occurred in the potentials of sensor 100 in the same period where inputs to the logic means indicates a substantially constant sensed component concentration for the period, then a correction factor of 1.10 (110%) in a simple ratio could be applied to the currently sensed potential across sensor 100 before application of the logic means of mathematical conversion of the potential to sensed gas component concentration.

The above design disclosures present the skilled person with considerable and wide ranges from which to choose appropriate obvious modifications for the above examples. However, the objects of the present invention will still be obtained by the skilled person applying such design disclosures in an appropriate manner.

We claim:

1. A gas sensor for oxides of nitrogen assembly comprising:
   (a) an electrolyte comprising:
      (i) one or more alkali metal nitrates;
      (ii) one or more alkaline earth metal nitrates; and
      (iii) one or more reference electrode metal halogens, wherein the reference electrode metal of the reference electrode metal halogens is chosen from the group consisting of ruthenium, rhodium, palladium, rhenium, osmium, iridium, platinum and gold and the halogens of the reference metal halogens are chlorine, bromine or iodine;
   (b) the electrolyte in electrochemical connection between a sensing electrode and a reference electrode, whereby the reference electrode consists of a first reference electrode metal and the sensing electrode consists of any other reference electrode metal; and
   (c) the electrolyte and electrodes are supported on a substrate.

2. The sensor of claim 1 wherein the concentration of alkali metal nitrates is greater than about 20 weight percent of the total weight of alkali metal nitrates, alkaline earth metal nitrates, and reference electrode metal halogens.

3. The sensor of claim 1 wherein the concentration of reference electrode metal halogens is greater than about 0.005 weight percent of the total weight of alkali metal nitrates, alkaline earth metal nitrates, and reference electrode metal halogens.

4. The sensor of claim 1 wherein a circuit connection is made between the electrodes, such that a voltage across the electrodes and the electrolyte is capable of being measured.

5. The sensor of claim 1 wherein the electrolyte is sealed against a gas environment such that its gas components pass through a composite membrane to the electrolyte and the composite membrane is capable of substantially excluding one or more non-sensed gas components.

6. The sensor of claim 5 wherein the composite membrane has a hydrophobic layer sealing a support layer against the gas environment.

7. The sensor of claim 6 where the hydrophobic layer is a fluorine-containing polymer.

8. The sensor of claim 5 where the support layer comprises dessicant material.

* * * * *